United States Patent [19]

Carnahan, Jr.

[11] 4,160,110
[45] Jul. 3, 1979

[54] METHOD FOR STABILIZING BISPHENOLS UNDER MELT OR DISTILLATION CONDITIONS

[75] Inventor: James C. Carnahan, Jr., Schenectady, N.Y.

[73] Assignee: General Electric Company, Schenectady, N.Y.

[21] Appl. No.: 896,636

[22] Filed: Apr. 17, 1978

[51] Int. Cl.² ............................................. C07C 37/22
[52] U.S. Cl. ....................................... 568/703; 203/6; 568/702; 568/723; 568/724; 568/727; 568/728
[58] Field of Search ..................... 568/702, 703; 203/6

[56] References Cited
U.S. PATENT DOCUMENTS

| 2,672,485 | 3/1954 | Menn et al. ........................... 568/702 |
| 3,403,186 | 9/1968 | Schlichting et al. .................. 568/702 |

FOREIGN PATENT DOCUMENTS

| 664574 | 6/1963 | Canada ..................................... 568/702 |
| 1200319 | 4/1966 | Fed. Rep. of Germany. |
| 45-22539 | 7/1970 | Japan. |
| 48-97854 | 12/1973 | Japan. |
| 717634 | 10/1954 | United Kingdom ..................... 568/703 |
| 890432 | 2/1962 | United Kingdom. |

*Primary Examiner*—Norman Morgenstern
*Attorney, Agent, or Firm*—William A. Teoli; Joseph T. Cohen; Charles T. Watts

[57] ABSTRACT

A process is provided for improving the stability of bisphenols under melt or distillation conditions by employing an aromatic anhydride such as phthalic anhydride as a stabilizing agent. A reduction is effected in the rate of formation of phenol and other cracking products which are decomposition by-products of the bisphenol.

8 Claims, 1 Drawing Figure

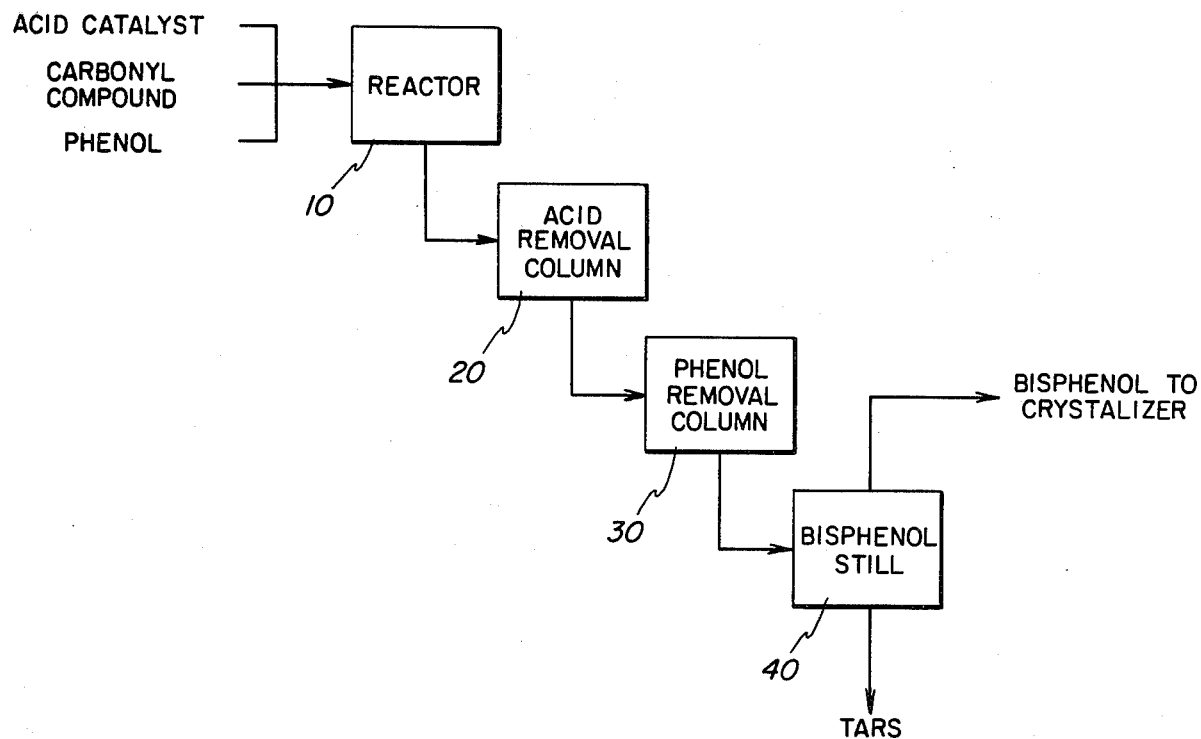

METHOD FOR STABILIZING BISPHENOLS UNDER MELT OR DISTILLATION CONDITIONS

BACKGROUND OF THE INVENTION

Bisphenols, such as diphenylol propanes can be made by initially effecting reaction between a phenol and an alkyl ketone, such as acetone, in the presence of a mineral acid, for example, hydrogen chloride, as shown by "Purification Key Step in Making Bisphenol-A", European Chemical News, pages 38–40, July 16, 1965. There is also shown a subsequent acid removal step and a phenol removal step. In the course of isolating the diphenylol propane, a distillation step is required to effect the separation of volatiles. The final bisphenol is recovered by crystallization. Experience has shown that in the course of manufacturing or isolating bisphenols in the molten state or under distillation conditions, breakdown of the bisphenol often occurs resulting in the production of phenol and other decomposition by-products.

As taught in British Pat. No. 890,432, directed to Thermo-Stabilized Dihydroxydiarylalkanes and Cycloalkanes, various inorganic or organic compounds, such as secondary or tertiary alkaline earth phosphates, stannous oxalate, stannous oxide, tin dioxide, terephthalic acid, isophthalic acid, oxalic acid, etc., boron trioxide, antimony trioxide, etc., can be used as complexing agents to react with impurities to minimize the effect of such impurities on the decomposition of bisphenols under melt or distillation conditions. It is specifically taught that phthalic acid, due to its tendency to pass over to the anhydride at elevated temperatures, is not effective as a bisphenol stabilizing agent. Japanese patent SHO-45-22539 teaches that an aliphatic dicarbonylic acid ester can be added to a bisphenol-A distillation mixture to depress the decomposition and undesirable coloring of bisphenol-A. In addition, Japanese patent SHO-45-22539 teaches that high purity diphenylol propane can be obtained by heating the crude reaction product with materials such as polypropylene glycols, epoxy resins and epoxidized soybean oils.

STATEMENT OF THE INVENTION

The present invention is based on the discovery that, contrary to the teaching of British Pat. No. 890,432, phthalic anhydride and certain phthalic anhydride derivatives can be utilized as stabilizers for bisphenol, while the bisphenol is being distilled, or while the bisphenol is in the form of a melt if the phthalic anhydride is used in an effective amount.

There is provided by the present invention, a method of stabilizing bisphenol during its manufacture involving the distillation of the melt of the reaction product of a phenol, a carbonyl compound selected from aldehydes and ketones and a mineral acid, which distillation normally results in breakdown of the resulting bisphenol to a significant degree, and an increase in the formation of phenol and substituted phenol as decomposition by-products, the improvement which comprises distilling the bisphenol reaction product in the presence of an effective amount by weight thereof of an organic anhydride selected from phthalic anhydride and phthalic anhydride derivatives, thereby stabilizing the bisphenol reaction product against decomposition under melt or distillation conditions by effecting a reduction in the rate of formation of phenol and substituted phenol as decomposition products.

The bisphenols which can be stabilized in the practice of the invention include bisphenols of the formula,

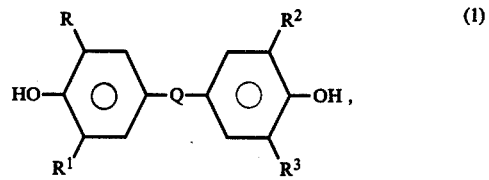

where $R$–$R^3$ are selected from hydrogen and the same or different $C_{(1-8)}$ alkyl radicals, such as methyl, ethyl, propyl, butyl, etc., Q is selected from 1,1-cyclopentyl, 1,1-cyclohexyl and —$C_yH_{2y}$—, and y is an integer equal to 1 to 5 inclusive. In addition to bisphenol-A, other bisphenols included within formula (1) are shown, for example, by Herman Schnell, Interscience Publishers, John Wiley and Sons, New York (1965) on page 69 of Chemistry and Physics of Polycarbonates.

In addition to phthalic anhydride, other organic anhydrides which can be used are, for example, tetrahydrophthalic anhydride and substituted phthalic anhydrides shown within the formula,

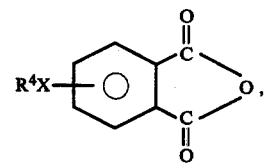

where $R^4$ is selected from a $C_{(1-8)}$ alkyl radical, a $C_{(6-13)}$ aromatic radical or $C_{(4-15)}$ aralkyl radical and X is selected from O and S. This class of compounds can be readily synthesized by methods described by F. J. Williams et al, J. Org. Chem. 45 3425 (1977). Organic dianhydrides such as 2,2-bis[4-(2,3-dicarboxyphenoxy)-phenyl]propane dianhydride, also can be used as a stabilizer.

The drawing is a typical schematic diagram showing various stages used in bisphenol manufacture. There is shown, for example, a reactor stage, an acid removal stage, a phenol removal stage and a bisphenol distillation stage.

More particularly, there is shown at 10, a reactor in which the mixture of carbonyl compound, for example, aldehydes, such as formaldehyde, acetaldehyde, butyraldehyde, etc., or ketone, such as acetone, methylethyl ketone, diethyl ketone, cyclohexanone, etc., and phenol or $C_{(1-8)}$ alkyl or dialkyl-substituted phenol can be heated in the presence of a mineral acid, such as hydrochloric acid. The removal of water and mineral acid can be achieved at 20 utilizing a distillation column. The residue is then fed into a distillation column at 30 to effect the removal of phenol and the resulting residue is then fed into the bisphenol distillation column at 40, followed by conveying the resulting distilled bisphenol to a bisphenol crystallizer.

In the practice of the invention, the bisphenol is distilled in the presence of an effective amount of phthalic anhydride or phthalic anhydride derivative, hereinafter referred to as "stabilizer", at a temperature in the range of from 230° C. to 290° C.

The stabilizer can be introduced into the bisphenol reaction product at the reactor stage as a solid or melt, or it can be introduced at a subsequent stage as a melt.

Preferably, the stabilizer is introduced prior to the distillation of the bisphenol and after the phenol removal column. The effective stabilization of the bisphenol under melt or distillation conditions can be achieved if the stabilizer is introduced on stream at such a rate as to provide during the distillation of the bisphenol, a bisphenol melt having a concentration of from 100 ppm to 20,000 ppm of stabilizer and preferably from 1000 ppm to 2000 ppm. In addition to resulting in an improvement in the yield of the bisphenol and a reduction in the level of phenol by-product, the stabilizer also has been found effective for reducing the level of substituted isomers such as isopropenylphenyl, the corresponding dimer, o,p-bisphenol, etc.

In order that those skilled in the art will be better able to practice the invention, the following examples are given by way of illustration and not by way of limitation. All parts are by weight.

EXAMPLE 1

Reaction is effected by stirring a mixture of 10 parts of acetone and 80 parts of phenol at 50° C. under 15 psi of anhydrous hydrogen chloride. The reaction is continued until the mixture is found to be free of acetone, based on the periodic analysis of a titer of the mixture. At the termination of the condensation reaction, the mixture is then distilled to effect the removal of excess acid and water. The resulting residue is then distilled under reduced pressure to effect the removal of phenol. The resulting crude bisphenol-A is further purified by distillation, followed by crystallization.

Various materials were then evaluated as potential stabilizers for the above bisphenol-A. Each of the materials was utilized with the bisphenol-A in an amount sufficient to produce mixtures having 1% by weight of stabilizer. Each of the stabilized bisphenol-A mixtures was tested in the same 304 stainless steel reactor and heated under sealed conditions for 1 hour at 290° C. There was obtained various decomposition products such as phenol, isopropenylphenol and other isomers which were analyzed by high pressure liquid chromatography. The effectiveness of the stabilizer was measured in terms of the weight percent of the phenol generated. The following results were obtained.

| Stabilizer | phenol (weight %) |
|---|---|
| none | 3.7 |
| phthalic anhydride | 1.4 |
| tetrahydrophthalic anhydride | 1.6 |
| 1,4-bis(2,3-dicarboxyphenoxy)benzene dianhydride | 1.6 |
| zinc borate | 1.9 |
| phthalic acid | 2.0 |
| boric acid | 2.2 |
| polymethylvinyl ether-maleic anhydride copolymer | 2.8 |
| oxalic acid | 2.0 |
| tin powder | 2.5 |
| diethyl oxalate | 2.5 |
| adipic acid | 2.8 |
| isophthalic acid | 2.8 |

The above results show that organic anhydrides, and particularly phthalic anhydride and its derivatives are effective stabilizers for bisphenols under melt or distillation conditions.

EXAMPLE 2

There is added phthalic anhydride melt to a bisphenol-A manufacturing stream continuously flowing from the bottom of the phenol removal column and prior to its entry into the bisphenol-A distillation column. The parts per hour rate of phthalic anhydride melt introduced into the bisphenol-A stream is adjusted to provide a steady state concentration of about 1000 ppm of phthalic anhydride based on the weight of melt in the distillation column. It is found that there is an average of about 38 parts per hour of phenol generated during the distillation of the bisphenol-A melt containing the phthalic anhydride, as compared to an average of about 87 parts per hour of phenol generated from about the same weight of bisphenol-A melt substantially free of phthalic anhydride. In addition, there is also found that an average of about 13 parts per hour of isopropenylphenol is generated during the phthalic anhydride steady state period, as compared to an average of 35 parts per hour generated from the bisphenol-A under distillation conditions free of phthalic anhydride.

The above results establish that the phthalic anhydride stabilizer of the present invention is capable of substantially improving the stability of bisphenol-A under continuous distillation conditions in the presence of an effective amount of the stabilizer as compared to the continuous distillation of bisphenol-A free of stabilizer.

Although the above examples are directed to only a few of the very many variables within the scope of the present invention, it should be understood that the present invention is directed to the use of a much broader variety of phthalic anhydride stabilizers and to bisphenols which can be stabilized under melt or distillation conditions as shown by the description preceding these examples.

What I claim as new and desire to secure by Letters Patent of the United States is:

1. A method for stabilizing a bisphenol against decomposition while the bisphenol is in the molten state, or while it is being distilled, which comprises, heating the bisphenol in the presence of an effective amount of stabilizer selected from the group consisting of phthalic anhydride or a phthalic anhydride derivative.

2. A method in accordance with claim 1, where the bisphenol has the formula,

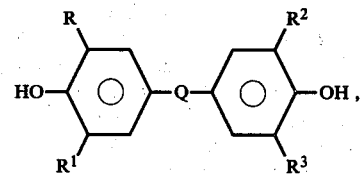

where $R$–$R^3$ are selected from hydrogen and the same or different $C_{(1-8)}$ alkyl radicals, Q is selected from 1,1-cyclopentyl, 1,1-cyclohexyl and —$C_yH_{2y}$—, and y is an integer equal to 1 to 5 inclusive.

3. A method in accordance with claim 2, where the bisphenol is bisphenol-A.

4. A method in accordance with claim 1, where the stabilizer is phthalic anhydride.

5. A method in accordance with claim 1, where the stabilizer is present at from 100 ppm to 20,000 ppm, based on the weight of molten bisphenol.

6. A method in accordance with claim 1, where the stabilizer is tetrahydrophthalic anhydride.

7. A method in accordance with claim 1, where the stabilizer is 2,2-bis[4-(2,3-dicarboxyphenoxy)phenyl]propane dianhydride.

8. In a method for stabilizing a bisphenol during its manufacture involving the distillation of the melt of the reaction product of a phenol and a carbonyl compound, selected from an aldehyde and ketone in the presence of a mineral acid which normally results in the breakdown of the resulting bisphenol reaction product to a significant degree and an increase in the formation of such phenol and substituted phenol as decomposition by-products resulting in a decrease in the yield of the bisphenol which involves the improvement comprising distilling the bisphenol reaction product in the presence of an effective amount of an organic anhydride selected from phthalic anhydride or phthalic anhydride derivatives, whereby the bisphenol reaction product is stabilized against decomposition under melt or distillation conditions.